United States Patent
O'Halloran et al.

(10) Patent No.: US 6,797,262 B2
(45) Date of Patent: Sep. 28, 2004

(54) FILM FORMING COMPOSITIONS FOR TOPICAL USE AND DELIVERY OF ACTIVE INGREDIENTS

(76) Inventors: David O'Halloran, c/o Lavipharm Laboratories Inc., 69 Princeton-Hightstown Rd., East Windsor, NJ (US) 09520; Yelena Zolotarsky, 62 Henshaw Ave., Springfield, NJ (US) 07081

(*) Notice: Subject to any disclaimer, the term of this patent is extended or adjusted under 35 U.S.C. 154(b) by 0 days.

(21) Appl. No.: 10/116,009

(22) Filed: Apr. 3, 2002

(65) Prior Publication Data

US 2003/0007944 A1 Jan. 9, 2003

(30) Foreign Application Priority Data

Apr. 4, 2001 (FR) .......................................... 01 04582

(51) Int. Cl.⁷ ................................................. A61K 7/48
(52) U.S. Cl. ...................... 424/78.03; 424/47; 424/401
(58) Field of Search ............................. 424/78.03, 401, 424/47

(56) References Cited

U.S. PATENT DOCUMENTS

| | | | |
|---|---|---|---|
| 5,120,529 A | | 6/1992 | Koch et al. |
| 6,106,813 A | | 8/2000 | Mondet et al. |
| 6,214,329 B1 | * | 4/2001 | Brieva et al. .............. 424/70.7 |
| 6,224,887 B1 | * | 5/2001 | Samour et al. ............. 424/401 |
| 6,277,364 B1 | * | 8/2001 | Bucks et al. ............. 424/78.03 |
| 6,306,411 B1 | | 10/2001 | Lezer |
| 6,352,699 B1 | * | 3/2002 | Mondet et al. ............. 424/401 |
| 6,372,230 B1 | * | 4/2002 | Schincaglia et al. ........ 424/401 |

FOREIGN PATENT DOCUMENTS

| | | |
|---|---|---|
| EP | 1 025 832 | 8/2000 |
| FR | 2 814 674 | 4/2002 |
| FR | 2 823 118 | 10/2002 |
| GB | 2 105 732 | 3/1983 |
| WO | WO 01/0397 | 2/2001 |
| WO | WO 02/39962 | 5/2002 |

OTHER PUBLICATIONS

Skin Care and Cosmetic Ingredients Dictionary, p. 206(1994).*
French International Search Report FR 0212347 dated May 26, 2003.
International Search Report PCT/FR02/01182 dated Aug. 22, 2002.

* cited by examiner

Primary Examiner—Jyothsna Venkat
(74) Attorney, Agent, or Firm—Dechert, LLP; John W. Ryan

(57) ABSTRACT

Cosmetic and/or therapeutic film former compositions for a topical use and for optional delivery of active ingredients to the skin are provided. More particularly, film forming compositions are provided, containing 1 to 50 wt % polyurethane, preferably polyurethane-1; at least 0.01 wt %, but less than 2.0 wt %, cellulose and 0.05 to 5.0 wt % magnesium aluminum silicate; wherein the film forming composition forms a uniform mist when discharged from a spray bottle or pump sprayer. A method for applying a film forming composition to an individual's skin is also provided including spraying the film forming composition onto the skin, wherein the film forming composition contains 1 to 50 wt % polyurethane; at least 0.01 wt %, but less than 2.0 wt %, cellulose and 0.05 to 5.0 wt % magnesium aluminum silicate; and wherein the film forming composition forms a uniform mist when sprayed.

8 Claims, No Drawings

FILM FORMING COMPOSITIONS FOR TOPICAL USE AND DELIVERY OF ACTIVE INGREDIENTS

The present invention claims priority from French Patent Application No. 0104582, filed Apr. 4, 2001.

The invention relates to a new cosmetic and/or therapeutic film former composition for a topical use, the invention also relates to the use of this film former composition for the delivery of active ingredients to the skin. More particularly, the present invention relates to film forming compositions, containing 1 to 50 wt % polyurethane, preferably polyurethane-1; at least 0.01 wt %, but less than 2.0 wt %, cellulose and 0.05 to 5.0 wt % magnesium aluminum silicate; wherein the film forming composition forms a uniform mist when discharged from a spray bottle or pump sprayer. The present invention also relates to a method for applying a film forming composition to an individual's skin by spraying the film forming composition onto the skin, wherein the film forming composition contains 1 to 50wt % polyurethane, preferably polyurethane-1; at least 0.01 wt %, but less than 2.0 wt %, cellulose and 0.05 to 5.0 wt % magnesium aluminum silicate; and wherein the film forming composition forms a uniform mist when sprayed. The present invention also relates to a method for treating a dermatological disease by applying to the skin of an individual a film forming composition of the invention containing an active agent for such treatment.

Conventional cosmetic or therapeutic compositions permit the application of active agents to the skin. However, an application at skin level must resist environmental conditions and clothes friction. Conventional compositions exhibit poor resistance to such environmental conditions and must be reapplied frequently to achieve the desired purpose (cosmetic or therapeutic). For example, in cosmetology, the use of cellulose and clay to suspend particles is conventionally practiced. The films resulting from these conventional compositions, however, are often easily removed with a combination of friction and water. Moreover, these films tend to be very dry and powdery.

Applicant's have developed a film forming composition for topical use which solves the above-mentioned problems with the conventional compositions. The film forming compositions of the present invention, when applied to the skin, dry to a smooth, uniform and distinctive film, which may be visible or invisible depending on the specific application, which is comfortable to wear and which resists environmental conditions such as rain and slight friction.

The film forming compositions of the present invention provide a method for delivering active agents to the skin of an individual. Particularly, the film forming compositions of the present invention provide improved contact times and for controlled release.

SUMMARY OF THE INVENTION

In a preferred embodiment of the present invention, film forming compositions are provided, containing: 1 to 50 wt % polyurethane, preferably polyurethane-1; at least 0.01 wt %, but less than 2.0 wt %, cellulose and 0.05 to 5.0 wt % magnesium aluminum silicate. In a preferred aspect of the invention, the film forming composition forms a uniform mist when discharged from a spray bottle or pump sprayer.

In a preferred aspect of the present invention, the cellulose contained in the film forming compositions is hydroxypropyl methylcellulose.

In another preferred aspect of the present invention, the film forming compositions further contain an active agent, more preferably 0.01 to 10 wt % active agent. Preferably, the active agent is selected from the group of a therapeutic agent, a cosmetic agent and mixtures thereof. The active agent may also preferably be selected from the group of a hydrophilic ingredient, a lipophilic ingredient and mixtures thereof. More preferably, the active agent may be selected from the group of alpha-hydroxy acids, beta-hydroxy acids, alpha-hydroxy acid derivatives, beta-hydroxy acid derivatives, botanical extracts, botanical extract derivatives, vitamins, vitamin salts, vitamin esters, vitamin alcohols, acid forms of salts, marine products, marine product derivatives, hormones and enzymes.

In another preferred aspect of the present invention, the film forming compositions further contain an ingredient selected from the group of hydrophilic solvents, lipophilic solvents, humectants/plastisizers, thickening polymers, dyes, colorants, surfactants/emulsifiers, fragrances, preservatives, chelating agents, UV absorbers/filters, antioxidants, keratolytic agents, dihydroxyacetone and penetration enhancers; wherein the thickening polymers are in addition to the polyurethane and the cellulose. Preferably, the film forming compositions of the present invention may contain 5 to 90 wt % hydrophilic solvents. Preferably, the film forming compositions of the present invention may contain 1 to 10 wt % lipophilic solvent. Preferably, the film forming compositions of the present invention may contain 0.5 to 20 wt % humectants/plastisizers. Preferably, the film forming compositions of the present invention may contain 0.1 to 10 wt % thickening polymers. Preferably, the film forming compositions of the present invention may contain 0.1 to 10 wt % surfactants/emulsifiers. Preferably, the film forming compositions of the present invention may contain 0.01 to 12 wt % pigments, dyes and colorants. Preferably, the film forming compositions of the present invention may contain 0.1 to 5 wt % fragrances. Preferably, the film forming compositions of the present invention may contain 0.01 to 3 wt % preservatives. Preferably, the film forming compositions of the present invention may contain 0.01 to 1 wt % chelating agent. Preferably, the film forming compositions of the present invention may contain 0.01 to 10 wt % UV absorbers/filters. Preferably, the film forming compositions of the present invention may contain 0.05 to 3wt % antioxidants.

In another preferred embodiment, the film forming compositions of the present invention may preferably be formulated for topical use as a liquid, a semi-solid lotion or a semi-solid gel. Most preferably this composition will either be a spray, a lotion, a gel, a roll-on or a mousse.

In another preferred embodiment of the present invention, a method of applying a film on an individual's skin is provided, which method includes: (1) spraying a film forming composition onto the skin, wherein the film forming composition contains 1 to 50 wt % polyurethane, preferably polyurethane-1; at least 0.01 wt %, but less than 2.0 wt %, cellulose and 0.05 to 5.0 wt % magnesium aluminum silicate; and wherein the film forming composition forms a uniform mist when sprayed. In a preferred aspect of this embodiment of the present invention, the method further includes: allowing the film forming composition to dry on the skin and wearing the dry film for 20 minutes to several hours, more preferably 20 minutes to four hours. In another preferred aspect of this embodiment, the film forming composition further contains an active agent for treatment of a dermatological disease, preferably a dermatological disease selected from the group of acne, psoriasis and eczema.

In another preferred embodiment of the present invention, a method of applying and fixing pigments, dyes or colorants onto the skin is provided, which method includes: spraying a film forming composition onto the skin, wherein the film forming composition contains 1 to 50 wt % polyurethane, preferably polyurethane-1; at least 0.01 wt %, but less than 2.0 wt % cellulose; 0.05 to 5.0 wt % magnesium aluminum silicate and 0.01 to 12 wt % pigments, dyes and/or colorants; wherein the film forming composition forms a uniform mist when sprayed. In a preferred aspect of this embodiment of the present invention, the method further includes: allowing the film forming composition to dry on the skin and wearing the dry film for 20 minutes to several hours, more preferably 20 minutes to eight hours, most preferably 20 minutes to several hours.

DETAILED DESCRIPTION

The present invention provides a film forming composition for topical use which includes a polymeric system containing polyurethane, cellulose and magnesium aluminum silicate.

Polyurethane suitable for use with the invention includes copolymers of isophtalic acid, adipic acid, hexylene glycol, neopentylene glycol, dimethylolpropanic acid and isophoronic diisocyanate monomers. Most preferably, the polyurethane used with the invention includes polyurethane-1.

The film forming compositions of the present invention exhibit the capacity to release active agents to the skin level. Applicants have discovered that magnesium aluminum silicate, polyurethane and cellulose form a synergistic combination. Used individually, each of magnesium aluminum silicate, polyurethane and cellulose tend to dry and flake. When combined in the film forming compositions of the present invention, these components provide a unique formula which exhibits increased stability.

Moreover, cellulose based compounds are generally not suited for spray application from a spray bottle or pump sprayer. The polymer combination of the present invention, however, provides a composition which is suited for spray application. Specifically, the polymer combination of the present invention provides a composition which forms a uniform mist when sprayed.

The film forming compositions of the present invention preferably contain:
from 1 to 50% by weight polyurethane, more preferably from 3 to 30%,
from 0.01 to 2.0% by weight cellulose, more preferably from 0.01 to 1.0%,
from 0.05 to 5.0% by weight magnesium aluminum silicate, more preferably from 0.1 to 3.0%.

When the polyurethane content is below 3%, the resulting film forming compositions do not form a sufficiently distinctive film. When the cellulose content is above 1.0%, the resulting film forming composition begins to exhibit unfavorable spraying characteristics and the resultant film tends to be both weak and breakable. When the magnesium aluminum silicate content is below 0.1%, the efficiency of the suspending effect of particles deminishes. When the magnesium aluminum silicate content is above 3.0%, the resultant film becomes brittle.

Cellulose suitable for use with the present invention includes any kind of cellulose, such as hydroxypropyl methylcellulose or hydroxyethyl cellulose. Preferably, the cellulose contained in the film forming compositions of the present invention is hydroxypropyl methylcellulose.

The film forming compositions of the present invention preferably provide a system for the delivery of an active agent at the skin level. Consequently, preferable film forming compositions of the present invention contain an active agent, more preferably 0.01 to 10% by weight of an active agent. Preferably, the active agent is selected from the group of therapeutic agents, cosmetic agents and mixtures thereof. The active agents may include natural or synthetic, hydrophilic agents or lipophilic agents.

Active agents suitable for use with the present invention include: alpha-hydroxy acids; alpha-hydroxy acid derivatives; beta-hydroxy acids; beta-hydroxy acid derivatives; botanical extracts; botanical extract derivatives; vitamins such as vitamins C, B, E, K or A or the salts, esters, alcohols or acid forms thereof; marine products; marine product derivatives; hormones and enzymes.

The film forming compositions of the present invention may further optionally contain additional components including: hydrophilic solvents, lipophilic solvents, humectants/plastisizers, thickening polymers others than cellulose and polyurethane, dyes, colorants, surfactants/emulsifiers, fragrances, preservatives, chelating agents, UV absorbers/filters, antioxydants, keratolytic agents, dihydroxyacetone and penetration enhancers.

The film forming compositions of the present invention may preferably contain 5 to 90% by weight hydrophilic solvents. Hydrophilic solvents suitable for use with the present invention include any solvent conventionally used in cosmetology or in dermatology. Preferred hydrophilic solvents suitable for use with the present invention include: water; alcohols (for example, ethanol, glycols and mixtures thereof).

The film forming compositions of the present invention may preferably contain 1 to 10% by weight lipophilic solvents. Lipophilic solvents suitable for use with the present invention include solvents such as hydrocarbons and oils. Preferred lipophilic solvents suitable for use with the present invention include: iso-paraffin, mineral oils, isododecane, sweet almond oil and other natural oils.

The film forming compositions of the present invention may preferably contain 0.5 to 20% by weight humectants/plastisizers. Humectants/plastisizers suitable for use with the present invention include any water-binding ingredient conventionally used in cosmetic or dermatological products. Preferred humectants/plastisizers suitable for use with the present invention include glycols (glycerin, propylene glycol, 1,3-butylene glycol and polyethylene glycols), dimethicone copolyol, sorbitol, sodium PCA, and sodium citrate.

The film forming compositions of the present invention may preferably contain 0.1 to 10% by weight thickening polymers other than cellulose and polyurethane. Thickening polymers suitable for use with the present invention include any polymer or thickener conventionally used in cosmetic or dermatological products. Preferred thickening polymers suitable for use with the present invention include xanthan gum; PVA; PVP; carbomer; and mixtures, such as: (a) ammonium polyacrylate, isohexadecane and polyethylene glycol-40 castor oil (an example of such a mixture suitable for use with the present invention is available from Seppic under the trademark Simulgel A); (2) polyacrylamide, polydecene and ethoxylated lauryl alcohol (an example of such a mixture suitable for use with the present invention is available from C. I. T. Sarl under the trademark Ceragel EZ-7); (3) polyacrylamide, $C_{13-14}$ isoparaffin and ethoxylated lauryl alcohol (an example of such a mixture suitable for use with the present invention is available from Seppic under the trademark Sepigel 305); and (4) polyquaternium 32 and mineral oil (an example of such a mixture suitable for use with the present invention is available from Ciba under the trademark Salcare SC-92). Thickeners may be added to the compositions of the present invention to modify the viscosity of the composition, the feel of the composition and the film formed therewith when applied to the skin of a subject, the spreadability of the composition and the strength of the film formed by the composition upon application to the skin of a subject.

The film forming compositions of the present invention may preferably contain 0.1 to 10% by weight surfactants/emulsifiers. Surfactants/emulsifiers suitable for use with the present invention include any anionic, cationic or nonionic surfactants or emulsifiers conventionally used in cosmetic or dermatological products. Preferred surfactants/emulsifiers suitable for use with the present invention include ethoxylated alcohols, sodium lauryl sulfate, and polyquaternium-31.

The film forming compositions of the present invention may preferably contain 0.01 to 12% by weight pigments, dyes and colorants. Pigments, dyes and colorants suitable for use with the present invention include any dye or pigment conventionally used in cosmetic, dermatological and food products. Preferred pigments, dyes and colorants suitable for use with the present invention include titanium dioxide; zinc oxides; iron oxide; micas, preferably pearlized micas; and organic lakes.

The film forming compositions of the present invention may preferably contain 0.1 to 5% by weight fragrance. Fragrance suitable for use with the present invention includes any fragrance conventionally used in cosmetic or dermatological products. Fragrance or fragrance mixtures may be incorporated into the film forming compositions of the present invention to, for example, support a marketing concept or to mask the natural odor of the subject composition.

The film forming compositions of the present invention may preferably contain 0.01 to 3% by weight preservative. Preservative suitable for use with the present invention includes any preservative or mixture of preservatives conventionally used in cosmetic or dermatological compositions. Preferred preservatives suitable for use with the present invention include methylparaben, isoporpylparaben, propylparaben, isobutylparaben, butylparaben and phenoxyethanol. Preservatives may preferably be incorporated in the film forming compositions of the present invention to enhance the resistance of said film forming compositions from microbiological contamination.

The film forming compositions of the present invention may preferably contain 0.01 to 1% by weight chelating agents. Chelating agents suitable for use with the present invention include any chelating agent conventionally used in cosmetic or dermatological products. Preferred chelating agents suitable for use with the present invention include ethylenediaminetetraacetic acid, ethylenediaminetetraacetic acid-disodium salt and ethylenediaminetetraacetic acid-tetrasodium salt. Chelating agents may preferably be incorporated into the film forming compositions of the present invention to help stabilize those compositions.

The film forming compositions of the present invention may preferably include 0.01 to 10% by weight UV absorbers/filters. UV absorbers/filters suitable for use in the film forming compositions of the present invention include any water and/or oil soluble sunscreen conventionally used in cosmetics. Preferred UV absorbers/filters suitable for use with the present invention include benzophenone-3 and benzophenone-4, titanium dioxide and zinc oxide.

The film forming compositions of the present invention may preferably include 0.05 to 3% by weight antioxidants. Antioxidants suitable for use in the film forming compositions of the present invention include any antioxidants conventionally used in cosmetics. Preferred antioxidants suitable for use with the present invention include tocopherol, tocopherol acetate, propyl gallate, butylated hydroxyanisole and butylated hydroxytoluene. Preferably, the as compositions of the present invention may contain 0.05 to 3 wt % antioxidants.

The film forming compositions of the present invention may preferably be for topical use and may advantageously be liquid or semi-liquid. Most preferably, the film forming compositions of the present invention may be a spray, a lotion, a gel or a roll-on.

Preferably, when a film forming composition of the present invention can be worn on the skin of a subject for a period of 20 minutes to several hours following application thereto as a dry film. Most preferably, the film forming compositions of the present invention may be removed from the skin of a subject by rinsing with water or with a combination of rinsing with water and use of a surfactant.

The present invention also provides a method of using a film forming composition for topical delivery of an active agent for the treatment of a dermatological disease, for example, acne, psoriasis and eczema. The active ingredient used in the cosmetic composition is chosen for its activity in the treatment of these dermatological diseases.

The present invention also provides a method of using a film forming composition of the present invention for topical use in a cosmetic product.

EXAMPLES

The preferred embodiments of the present invention will now be further described through the following examples set forth hereinbelow which are intended to be illustrative of the preferred embodiments of the present invention and are not intended to limit the scope of the invention as set forth in the appended claims.

Some preferred formulations for film forming compositions of the present invention are provided in Table 1. The film forming compositions of the present invention noted in Table 1 may be produced as follows: the polymers are blended in one of: water, alcohol or a mixture thereof. A supply of heat may be useful in preparing film forming compositions of the present invention which include clay or a gum. Polymers may be added one after the other with continual mixing until the mixture is smooth. The other ingredients may be added after the uniform polymer mixture is obtained. High sheer may preferably be used to incorporate UV absorbers/filters into the composition.

TABLE 1

| Ingredients | Example 1 A% (wt/wt) | Example 2 B% (wt/wt) | Example 3 C% (wt/wt) |
| --- | --- | --- | --- |
| Water | QS to 100 | QS to 100 | QS to 100 |
| Methylcellulose | 0.01 to 1.0 | 0.01 to 1.0 | 0.01 to 1.0 |
| Mg, Al silicate | 0.10 to 3.0 | 0.10 to 3.0 | 0.10 to 3.0 |
| Polyurethane | 3.0 to 30.0 | 3.0 to 30.0 | 3.0 to 30.0 |
| Alcohol | 0.1 to 30.0 | 0.1 to 30.0 | |
| Glycol (e.g., butylene, propylene, hexalene or glycerin or PEG) | 0.10 to 5.0 | 0.1 to 5.0 | 0.1 to 10.0 |
| Inorganic UV filters (e.g., titanium dioxide or zinc oxides) | 0.01 to 10.0 | | |
| UV Absorbers (e.g., benzophone-3 or 4, octyl salicylate, octyl methoxycinnamate) | 1.0 to 8.0 | | |

TABLE 1-continued

| Ingredients | Example 1 A% (wt/wt) | Example 2 B% (wt/wt) | Example 3 C% (wt/wt) |
|---|---|---|---|
| Preservatives | 0.01 to 3.0 | 0.01 to 3.0 | 0.01 to 3.0 |
| Active ingredient | 0.01 to 3.0 | 0.01 to 3.0 | 0.01 to 3.0 |
| Viscosity modifiers | 0.01 to 3.0 | 0.01 to 3.0 | 0.01 to 3.0 |
| pH adjusters (e.g., organic or inorganic acids, amines or hydroxides) | 0.01 to 3.0 | 0.01 to 3.0 | 0.01 to 3.0 |

Examples 4 and 5

Compositions of the present invention according to the formulas presented in Table 2 may be prepared according to Examples 4 and 5.

TABLE 2

| Ingredients | Example 4 (% w/w) | Example 5 (% w/w) |
|---|---|---|
| Water | QS | QS |
| Glycerin | 1.0 | |
| Biophilic H (Hydrogenated Lecthin, C12–16 Alcohols, Palmitic Acid) | 2.0 | |
| Methocel E4M (HPMC) | 0.20 | 0.20 |
| Veegum HV (Mg Al Silicate) | 0.45 | 0.30 |
| Carbomer | 0.15 | 0.15 |
| AMP Amino-methyl-propanol | 0.20 | 0.20 |
| Polyurethane | 20.0 | 10.0 |
| Dimethicone Copolyol | 0.50 | 0.50 |
| Preservative | 0.70 | |
| Mg Ascorbyl Phosphate | | 0.20 |
| Ethanol SDA 40-2 (190 proof) | | 9.0 |

The composition identified in Table 2 as Example 4 may be prepared as follows:

(a) the biophilic (commercially available from Lucas Meyer) is mixed with water under slow stirring at 70° C.;

(b) the glycerin is added to the product of (a) with continual slow stirring until a coarse and fluid dispersion is obtained; care is to be taken during this step to keep the temperature from falling below 50° C.;

(c) the methocel E4M (commercially available from Dow Chemical) is added to the product of (b) with continual mixing until it is completely hydrated;

(d) the Veegum HV (commercially available from R. T. Vandrbilt) is added to the product of (c) with continual mixing until it is completely hydrated;

(e) the carbomer (commercially available from Noveon) is added to the product of (d) with continual mixing until it is completely hydrated;

(f) the AMP (commercially available from Angus) is added to the product of (e) with continual mixing until a smooth uniform product is obtained;

(g) the polyurethane is added to the product of (f) with thorough mixing;

(h) the dimethicone copolyol is added to the product of (g) with thorough mixing; and, (i) the preservative is added to the product of (h) with thorough mixing.

The composition identified in Table 2 as Example 5 may be prepared as follows:

(a) the methocel E4M is mixed with water until fully hydrated;

(b) the veegum HV is mixed with the product of (a) until fully hydrated;

(c) the carbomer is mixed with the product of (b) until fully hydrated;

(d) the product of (c) is heated to about 50° C.;

(e) the AMP is added to the product of (d) and blended until smooth and uniform;

(f) the Mg Ascorbyl Phosphate is dissolved in water and heated to 40° C.;

(g) the product of (f) is blended with the product of (e);

(h) the polyurethane is added to the product of (g) with continual mixing;

(i) the dimethicone copolyol is added to the product of (h) with continual mixing;

(j) the ethanol CDA 40-2 is added to the product of (i) with continual mixing; and, (k) the preservative is added to the product of (j) with continual mixing until a uniform product is formed.

Examples 6–9

Table 3, below, provides various exemplary formulations of the film forming compositions of the present invention suitable for topical use as a make-up spray patch. The formulations presented in Table 3 include various amounts of different pigments. The formulations provided in Examples 6 and 8 relate to a film forming compositions of the present invention which contain iron oxides, titanium dioxide and nacreous pigments with dimethicone copolyol and cyclomethicone as the emollient/humectant system. The formulations provided in Examples 7 and 9 relate to a film forming compositions of the present invention which contain titanium dioxide, iron oxides, nacreous pigments and glycol as the emollient/humectant system.

TABLE 3

| Ingredient | Ex. 6 (% w/w) | Ex. 7 (% w/w) | Ex. 8 (% w/w) | Ex. 9 (% w/w) |
|---|---|---|---|---|
| Water | QS | QS | QS | QS |
| Methocel E4M (HPMC) | 0.32 | 0.20 | 0.32 | 0.50 |
| Veegum HV (Mg AL Silicate) | 0.90 | 0.45 | 0.90 | 1.20 |
| Carbomer | 0.15 | 0.10 | 0.15 | 0.20 |
| AMP (Aminomethyl propanol) | 0.20 | 0.20 | 0.20 | 0.30 |
| Polyurethane-1 (30% soln. in water and alcohol) | 18.00 | 12.00 | 18.00 | 25.00 |
| Dimethicone Copolyol and cyclomethicone | 5.00 | — | 4.00 | — |
| Glycol (Glycerin, Propylene Glycol, Butylene Glycol) | — | 2.00 | — | 4.00 |
| Biological Extracts | 0.70 | 1.00 | 0.70 | 2.00 |
| Preservative | 0.70 | 0.70 | 0.70 | 0.80 |
| Titanium Dioxide | 2.10 | 3.50 | 1.80 | 4.00 |
| Mica Pearl (Nacreous) | 0.20 | 0.10 | 1.00 | 0.50 |
| Iron Oxides | 1.70 | 1.40 | 1.20 | 2.50 |

Example 10

The formulations presented in examples 6–9 may be blended in water. Heat may optionally be provided if, for example, clay or a gum is used. The polymers may be added one after another with agitation until a smooth mixture is obtained using a standard mixer with a sheer selected according to the materials being incorporated. The remaining ingredients may be added to the smooth mixture. High sheer may be required to incorporate iron oxides and titanium dioxide into the composition.

The present invention having been disclosed in connection with the foregoing preferred embodiments and examples, additional embodiments will now be apparent to persons skilled in the art. The present invention is not intended to be limited to the preferred embodiments specifically mentioned, and accordingly reference should be made to the appended claims rather than the foregoing discussion, to assess the spirit and scope of the present invention in which exclusive rights are claimed.

We claim:

1. A film forming composition for topical use, comprising: 1 to 50 wt % neutralized, anionic, low molecular weight polyurethane having molecular weight of 10,000–15,000 g/mol; at least 0.01 wt %, but less than 2.0 wt %, cellulose, 0.05 to 5.0 wt % magnesium aluminum silicate, and a vitamin selected from the group consisting of A, B, C, E and K or Magnesium Ascorbyl Phosphate; wherein the film forming composition forms a uniform mist when discharged from a spray bottle or pump sprayer.

2. The film forming composition of claim 1, wherein the cellulose is hydroxypropyl methylcellulose.

3. The film forming composition of claim 1, wherein the vitamin or Magnesium Ascorbyl Phosphate comprises 0.01 to 10 wt % of the film forming composition.

4. The film forming composition of claim 1, further comprising at least one ingredient selected from the group consisting of: hydrophilic solvents, lipophilic solvents, humectants/plastisizers, thickening polymers, surfactants/emulsifiers, fragrances, preservatives, chelating agents, UV absorbers/filters, antioxidants, keratolytic agents, dihydroxyacetone and penetration enhancers; wherein the thickening polymers are in addition to the polyurethane, the cellulose and the magnesium aluminum silicate.

5. A film forming composition for topical use, comprising: 1 to 50 wt % neutralized, anionic, low molecular weight polyurethane having molecular weight of 10,000–15,000 g/mol; at least 0.01 wt %, but less than 2.0 wt %, cellulose, 0.05 to 5.0 wt % magnesium aluminum silicate and Magnesium Ascorbyl Phosphate; wherein the film forming composition forms a uniform mist when discharged from a spray bottle or pump sprayer.

6. The film forming composition of claim 5, wherein the cellulose is hydroxypropyl methylcellulose.

7. The film forming composition of claim 6, further comprising at least one ingredient selected from the group consisting of: hydrophilic solvents, lipophilic solvents, humectants/plastisizers, thickening polymers, surfactants/emulsifiers, fragrances, preservatives, chelating agents, UV absorbers/filters, antioxidants, keratolytic agents, dihydroxyacetone and penetration enhancers; wherein the thickening polymers are in addition to the polyurethane, the cellulose and the magnesium aluminum silicate.

8. A film forming composition for topical use, comprising: 1 to 50 wt % neutralized, anionic, low molar weight polyurethane having molecular weight of 10,000–15,000 g/mol; at least 0.01 wt %, but less than 2.0 wt %, cellulose, 0.05 to 5.0 wt % magnesium aluminum silicate, and any one of vitamin A, B, C, E or K; wherein the film forming composition forms a uniform mist when discharged from a spray bottle or pump sprayer.

* * * * *